United States Patent [19]

Bessalem et al.

[11] Patent Number: 5,659,072
[45] Date of Patent: Aug. 19, 1997

[54] PROCESS FOR THE MANUFACTURE OF ALKYL ACRYLATES BY DIRECT ESTERIFICATION

[75] Inventors: Jacqueline Bessalem, Saint-Avold; Michel Fauconet, Valmont; Christian Lacroix, Folkling; Nathalie Hess, Saint-Avold, all of France

[73] Assignee: Elf Atochem S.A., Puteaux, France

[21] Appl. No.: 491,670

[22] Filed: Jun. 19, 1995

[30] Foreign Application Priority Data

Jun. 17, 1994 [FR] France .................. 94 07453

[51] Int. Cl.$^6$ .................. C07C 67/48
[52] U.S. Cl. .................. 560/218
[58] Field of Search .................. 560/218

[56] References Cited

U.S. PATENT DOCUMENTS 4,280,009  7/1981  Erpenbach et al. .................. 560/205
4,833,267  5/1989  Nakashima et al. .................. 60/205

*Primary Examiner*—Paul J. Killos
*Attorney, Agent, or Firm*—Millen, White, Zelano & Branigan, P.C.

[57] ABSTRACT

An acrylic acid ester is manufactured by reaction of the said acid and an alcohol chosen from $C_5$ or above primary and secondary aliphatic monoalcohols, in the presence of an acid as esterification catalyst and of a polymerization inhibitor, the alcohol being capable of forming a heteroazeotrope with water, the water formed by the esterification reaction being entrained by distillation in a column in the form of a heteroazeotropic mixture with the alcohol, which mixture, containing an amount of unreacted acrylic acid, is then subjected, after condensation, to a separation in order to give an upper organic phase which is recycled to the head of the distillation column and a lower aqueous phase which is withdrawn; according to the invention, an extraction (for example in an extraction column EC) of the acrylic acid contained in the condensed heteroazeotropic mixture (M) intended for phase separation with an esterifying-alcohol-rich mixture, and the acrylic acid thus extracted is returned to the head of the distillation column (DC), as a constituent of the recycled organic phase, with an increase in the level of reflux into the distillation column (DC) relative to the natural reflux.

12 Claims, 2 Drawing Sheets

PROCESS FOR THE MANUFACTURE OF ALKYL ACRYLATES BY DIRECT ESTERIFICATION

BACKGROUND OF THE INVENTION

The present invention relates to improvement to the process for the manufacture of alkyl acrylates by direct esterification.

It is necessary in esterification processes, in order to achieve maximum conversion of the alcohol and the acid, to shift the following reaction equilibrium over to the right:

$$R\text{-}COOH + R'\text{-}OH \leftrightarrows R\text{+}COOR' + H_2O.$$

With this aim, the most commonly used process consists in distilling off the lightest product, in this case the water, as it is formed. In order to optimize the reaction kinetics, it is important to limit the water present in the reaction medium to the minimum, by extracting it as quickly as possible, in order to avoid any reverse reaction.

In particular, in the field of the synthesis of acrylic esters, which have the reputation of being thermally unstable (polymerization promoted by thermal effect), it is conventional and energetically less expensive to distil off the water in the form of an azeotrope having a lower boiling point.

The azeotrope may be a homo- or a heteroazeo-trope, forming a one- or two-phase system with water respectively. In the case of the distillation of a homoazeotrope, selectivity of the distillation column can only be provided for at the cost of the refluxing of some of this azeotropic mixture to the head of the column. This results in water being returned into the reaction medium, which decreases the kinetics of the esterification reaction.

In contrast, if the mixture is a heteroazeotrope, this may be separated into an upper organic phase and a lower aqueous phase in a decanter located at the head of the distillation column, and the refluxing necessary to ensure good selectivity in the column my be obtained by recycling the single organic phase. In this case, the water is usually withdrawn continuously at the bottom of the decanter.

The substance used to entrain the water of the reaction azeotropically is generally an immiscible solvent which forms an azeotrope with water, as is described in American patents U.S. Pat. No. 5,093,520 and U.S. Pat. No. 2,917,538; however, this process has the drawback of adding a new substance to the reaction mixture, which will have to be separated out afterwards and possibly purified before recycling upstream in the process.

The use of the esterifying alcohol as azeotroping solvent, particularly if it is immiscible with water, is also described, thereby avoiding the use of a new substance in the process.

In the case of the manufacture of acrylic esters of alcohols having a number of carbon atoms greater than or equal to 5, such as 2-ethylhexyl acrylate, described in American patent US Pat. No. 4,280,009, this process cannot be used in a simple manner alone. The heteroazeotrope formed by the ester-alcohol-water mixture has a high boiling point which is relatively close to that of acrylic acid. As a result, some of the acrylic acid distils at the same time as the water and the entraining alcohol. In general, for the esterification of alcohols having a boiling point higher than that of acrylic acid, the lightest compound (acrylic acid) is entrained in the vapors, especially when, at the end of the reaction, the amount of water to be extracted from the reaction medium, which is required to form the light azeotropic mixture, becomes very low.

The entrainment of acrylic acid thus becomes particularly considerable when quantitative conversion of the reactants is intended.

After separation, a large proportion of this acrylic acid is found in the aqueous phase, which gives rise to a loss of product and an increase in the organic pollution (COD) of the water discharged from the plant.

With reference to FIG. 1 of the attached diagram, it may be seen that, in an esterification performed according to the usual technique, the vapors condensed at the head of the distillation column (DC) during the reaction (heteroazeotropic mixture M) are collected in a decanter (D) where the mixture separates out into two phases. The upper organic phase (O) is returned by overflow (R) (natural refluxing) to the head of the column (DC). The aqueous phase (A) is, itself, withdrawn continuously via a valve (V) which regulates a constant interphase level in the decanter (D).

When this process is applied to the synthesis of heavy acrylates, the content of acrylic acid in the aqueous phase recovered after reaction is very large.

In order to decrease the entrainment of acrylic acid in the azeotrope distilled off during the reaction, the amount of backstreaming within the column may be increased by introduction of some of the esterifying alcohol to the head of this column, as is described in American patents U.S. Pat. No. 4,833,267 and U.S. Pat. No. 4,280,009, in Romanian patent RO-70,951 and in Japanese patent application JP-A-58,192,851.

This method requires the addition, via the head of the column, of a large proportion of alcohol relative to the total amount of alcohol required for the reaction, and the technique is insufficient for avoiding the distillation of acrylic acid in the case of a synthesis of 2-ethylhexyl acrylate, particularly when total conversion of the reactants is intended.

Moreover, American patent U.S. Pat. No. 4,076,950 describes an esterification process aimed at distilling off, during the reaction, an azeotropic mixture which is free of acrylic acid. In order to do this, the organic phase which has been freed beforehand of the starting alcohol by extraction with water, and which then essentially contains anhydrous ester, is refluxed to the column head. This procedure cannot be adapted in the case of esterification of heavy alcohols ($C_n$ alcohols where $n \geq 5$), on account of the very low solubilities of the alcohols in water.

The problem which the Applicant Company has sought to solve, in the synthesis of acrylates manufactured from alcohols having a number of carbon atoms greater than or equal to 5, by direct esterification, performed continuously or discontinuously in the absence of external azeotroping solvent, is that of minimizing the content of acrylic acid in the waste water discharged from the plant, in order to reduce the loss of this monomer and the organic pollution (COD) which it entails.

To this end, provision is made, in accordance with the present invention, to return the acrylic acid entrained during the distillation of the heteroazeotropic mixture to the head of the distillation column mounted over the reactor, after extraction of this acid contained in the reaction water with an esterifying-alcohol-rich mixture.

The subject of the present invention is thus a process for the manufacture of an acrylic acid ester by reaction of the said acid and an alcohol chosen from primary and secondary aliphatic monoalcohols having a number of carbon atoms greater than or equal to 5, in the presence of an acid as esterification catalyst and of a polymerization inhibitor, the alcohol being capable of forming a heteroazeotrope with water, the water formed by the esterification reaction being entrained by distillation in a column in the form of a heteroazeotropic mixture with the alcohol, which mixture, containing an amount of unreacted acrylic acid, is then subjected, after condensation, to a separation in order to give an upper organic phase which is recycled to the head of the distillation column and a lower aqueous phase which is withdrawn, characterized in that an extraction of the acrylic acid contained in the condensed heteroazeotropic mixture intended for phase separation is carried out with an esterifying-alcohol-rich mixture, and in that the acrylic acid thus extracted is returned to the head of the distillation column, as a constituent of the recycled organic phase, with an increase in the level of backstreaming in the distillation column relative to the natural refluxing.

Various means allow this increase in the level of reflux in the distillation column, these means possibly depending in particular on whether continuous or discontinuous conditions are used.

Figure 1:
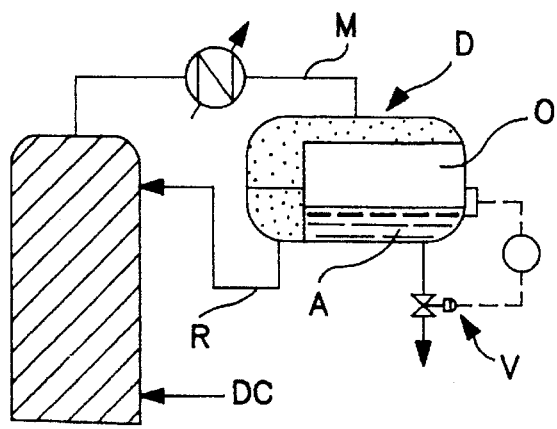
FIG. 1 illustrates schematically an esterification performed according to the state-of-the-art.
Figure 2:
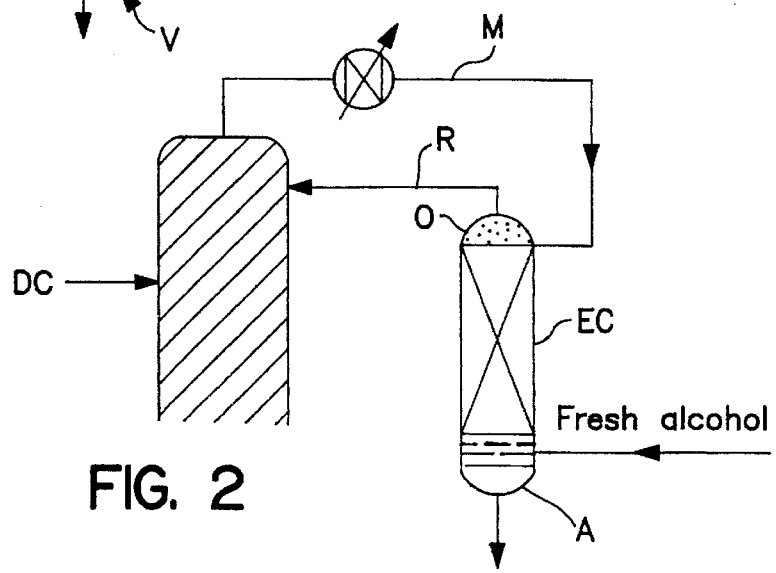
FIG. 2 illustrates schematically a first embodiment of the process according to the present invention, wherein the esterification is carried out continuously and the extraction operation is carried out in an extraction column.

In accordance with a first embodiment of the process according to the invention, illustrated schematically in FIG. 2, the esterification is carried out continuously, and the extraction operation is carried out in an extraction column (EC) supplied, at the head, with the condensed heteroazeotropic mixture (M), and, at the foot, with fresh alcohol.

Figure 3:
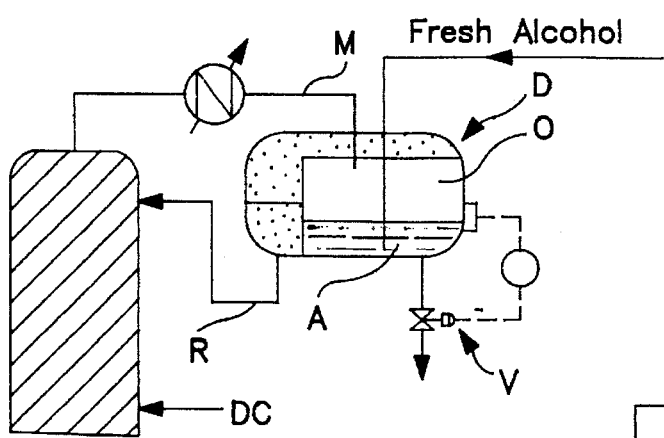
FIG. 3 illustrates schematically a second and a third embodiment of the process according to the present invention, wherein the esterification is carried out continuously or discontinuously respectively, and the extraction operation is carried out in a decanter.

In accordance with a second embodiment of the process of the invention, illustrated schematically in FIG. 3, the esterification is carried out continuously, and the extraction operation is carried out in a decanter (D) supplied, in the upper part of its supernatant organic phase (O), with the condensed heteroazeotropic mixture (M), and, in the lower part of its lower aqueous phase (A), with fresh alcohol, and the process is per formed so as to withdraw at constant interphase level in the decanter (D).

In accordance with a first embodiment of the process of the invention, also illustrated schematically in FIG. 3, the esterification is carried out discontinuously, by performing the process described in the above paragraph.

Figure 4:
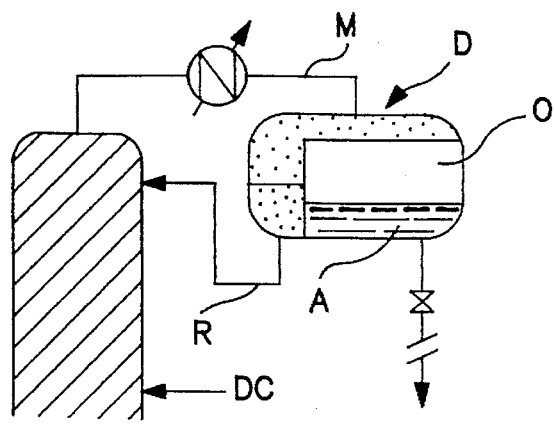
FIG. 4 illustrates schematically a fourth embodiment of the present invention, wherein the esterification is carried out discontinuously and the extraction operation is carried out in a decanter.

In accordance with a fourth embodiment of the process of the invention, illustrated schematically in FIG. 4, the esterification is carried out discontinuously, and the extraction operation is carried out in a decanter (D) of such a size as to be able to receive at least all of the heteroazeotropic mixture (M) without withdrawing at the bottom of the said decanter (D); before starting the reaction, the decanter (D) of esterifying alcohol is filled to the overflow level in the distillation column (DC); the condensed heteroazeotropic mixture (M), which is led into the upper part of the organic phase (O) which forms in the decanter (D), is accumulated in the latter for all or part of the reaction, the volume of upper organic phase (O) displaced by the volume of accumulated heteroazeotropic mixture being refluxed (by R) to the head of the distillation column (DC); and when the reaction is complete, the lower aqueous phase (A) is withdrawn and the volume of the heteroazeotropic mixture removed is replaced by fresh alcohol for a subsequent esterification reaction.

In accordance with a fifth embodiment of the process of the invention, the esterification is carried out discontinuously, by performing the process described in the above paragraph, the only difference being that fresh alcohol is introduced into the decanter for all or part of the reaction.

The alcohol/water heteroazeotropic mixture has a very water-rich (90% by volume) and alcohol-poor (10%) composition. As a result, by withdrawing the water with regulation of the interphase level in the decanter, the volume refluxed into the column represents 10% of the liquid derived from the condensed vapors. In accordance with the invention, by increasing this natural reflux by continuous introduction of fresh alcohol into the decanter (continuous or discontinuous process) and/or by accumulating the water without withdrawal at the foot of the decanter throughout the reaction (discontinuous process), the level of refluxing in the distillation column is increased. In the case of the process according to the invention for the discontinuous esterification with delayed withdrawal of the reaction water, at least all (100%) of the volume of, liquid (organic phase+aqueous phase) condensed is refluxed to the column head (delayed withdrawal without continuous introduction of fresh alcohol). This thus amounts to multiplying the amount of liquid refluxed into the column by a factor at least equal to 10, and thus to improving its selectivity.

In the process according to the invention, the decanter or the liquid—liquid extraction column allows the acrylic acid entrained in the reaction water to be reextracted. The vapors leaving the column are condensed and the liquid separates out into two phases. The aqueous phase crosses the mass of fresh alcohol present in the decanter before reaction or in the upper phase of the organic phase of the column, and by virtue of its coefficient of partition which is favorable to the alcoholic phase, a large part of the acrylic acid contained in this aqueous phase passes into the organic phase. Moreover, the continuous addition of alcohol into the lower aqueous phase of the decanter (continuous or discontinuous process) or of the extraction column (continuous process) makes it again possible to extract the acrylic acid in this aqueous phase.

The aqueous phase (E) obtained in the process of the invention is then sent, advantageously with other water from the plant (water from neutralization of the reaction crude, water from washing of the neutralized crude, water from trapping of the gas vents, etc.), into a downstream distillation column which enables the light organic products at the head to be recovered and the waste water at the foot to be discharged. The COD representing the acrylic acid entrained during the reaction is then markedly reduced relative to a process carried out at constant interphase level without further addition of fresh alcohol into the decanter.

In accordance with the present invention, it is also advantageously possible to carry out in the washing column an extraction of the final traces of acrylic acid contained in the aqueous phase obtained after the separation operation, with the reaction crude freed of the catalyst and of all or part of the acrylic acid by neutralization.

This improvement has several advantages:

- it makes it possible to reduce the organic pollution, in the form of COD due to the acrylic acid, discharged at the foot of the column for the distillation of the water of the plant;
- for esters whose boiling point is higher than that of acrylic acid, such as 2-ethylhexyl acrylate, it makes it possible to recover the residual acrylic acid entrained in the reaction water, in the light fractions of the forerun-removing column, for recycling to the reaction step;
- by being substituted for an addition of pure water, it decreases the water consumption of the plant, and consequently the amount of discharged water to be treated.

The esterification reaction is generally carried out at a temperature from 80° to 130° C., at normal pressure or at reduced pressure. 2-Ethylhexanol may be mentioned as an example of the alcohol.

Figure 5:
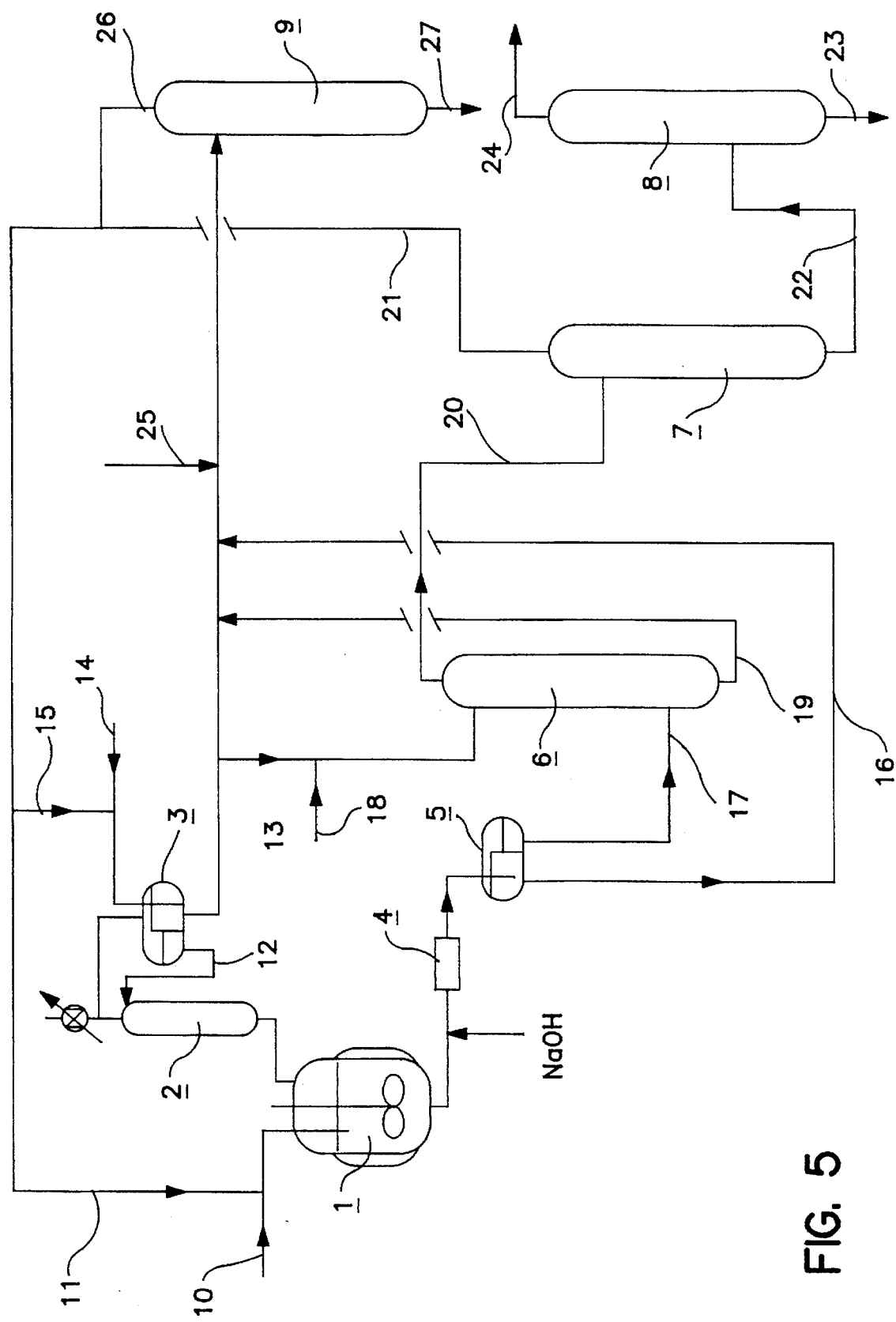
FIG. 5 is a flow sheet of a specific embodiment of the process for the manufacture of an acrylic acid ester according to the present invention.

In the attached drawing, apart from FIGS. 1 to 4 which have already been described, FIG. 5 represents a diagram of a specific embodiment of the process according to the invention, which will now be described.

Fresh acrylic acid, the fresh alcohol, the stabilizers and the catalyst ($H_2SO_4$) are introduced (discontinuously or continuously) via line 10 into the reactor 1 over which is mounted a distillation column 2, as well as the flow of light compounds (essentially alcohol and ester) recovered in the subsequent forerun-removing columns, via line 11. The temperature of the reaction medium is between 80° and 130° C., preferably between 80° and 100° C., at a pressure which is reduced so as to maintain the desired temperature. During the reaction, a mixture of alcohol, ester, water and acrylic acid is distilled off, and is separated out, after condensation, into two phases in the decanter 3. The organic phase 12 is returned by overflow to the head of column 2, whereas the aqueous phase 13 is sent to the supply of distillation column 9 and/or to the head of washing column 6. During the reaction, a flow of fresh alcohol and/or of light compounds 15 recovered from the forerun-removing columns is introduced into the decanter 3, via the pipe 14.

After reaction, the reaction crude is neutralized with aqueous sodium hydroxide solution in the mixer 4 in order to remove the catalyst and/or the residual acrylic acid. The heterogeneous mixture is separated out in the decanter 5 into an aqueous phase 16 which is sent to the supply of the column 9 and an organic phase which constitutes the supply at the foot of the washing column 6.

This washing column 6 is, moreover, supplied at the head with demineralized water 18 and/or all or some of the reaction water 13. At the column foot 6, an alkaline aqueous flow 19 is recovered, which rejoins the supply of column 9.

At the head of column 6, the neutralized and washed crude 20 is sent to the forerun-removing column 7, which makes it possible to recover at the head the excess alcohol and the acrylic acid extracted from the reaction water, as well as some ester. This mixture 21 is recycled to the reaction step via line 11.

The forerun-removed crude 22 recovered at the foot of column 7 feeds the residue-removing column 8, which removes the heavy fractions 23 at the foot, in order to obtain the pure ester 24 at the head.

All the aqueous phases of the plant: reaction water 13, water from neutralization of the crude 16, water from the washing column 19, other water of the plant 25, are sent onto column 9, at the head (26) of which is mainly recovered the alcohol, which is recycled to the reaction step via pipe 11. The waste water 27, freed of the bulk of the pollutant organic products, are removed for subsequent biological treatment before discharging.

The present invention will now be further illustrated by examples which are given by way of illustration and without any limitation being implied. In these examples, the percentages are by weight except where otherwise indicated, and the following abbreviations have been used:

AA=acrylic acid

2EHOH=2-ethylhexanol 2EHA=2-ethylhexyl acrylate

EXAMPLES 1 to 5

The process is performed discontinuously in apparatus consisting of:

- a heated reactor 150 liters in capacity, equipped with a mechanical stirrer, a temperature probe and an air inlet in order to provide gentle sparging in the reaction medium; an adiabatic column of 4theor- etical-plate efficiency is mounted over this reactor;
- a pipe which makes it possible optionally to send some of the esterifying alcohol and/or some of the ester to be recycled to the head of the column;
- a condenser supplied with a water-glycol mixture maintained at a temperature of 0° C.;
- a temperature measuring probe at the column head;
- a decanter receiving the condensed azeotrope, fitted with a system which makes it possible optionally to maintain a constant level of lower aqueous phase by automatically withdrawing the reaction water as it is formed by means of the opening of an electrovalve. The upper organic phase is returned to the column head by natural overflow. The inlet pipe of the condensed liquid leads into the upper part of the light phase, and a second pipe makes it possible optionally to send some of the esterifying alcohol and/or some of the ester to be recycled into the lower part of the heavy aqueous phase; and
- a regulated vacuum system which makes it possible to work at reduced pressure.

The following are charged into the reactor: The acrylic acid; the alcohol, in an amount such that the molar ratio of this compound to the initial acrylic acid is equal to 1.1 (for Example 5, some of the alcohol provided for the reaction is introduced continuously into the decanter, for all or part of the reaction); for Examples 3 to 5, an amount of ester 2EHA ranging between 15 and 20% relative to the total charge, in order to simulate the recycling of the ester-alcohol mixture recovered to the head of column 7 (flow 21); the phenothiazine stabilizer, added in an amount of 0.06% relative to the total charge; the sulphuric acid catalyst as a 95% solution, in an amount of 1% relative to the total charge.

Alcohol 2EHOH is introduced into the reaction decanter 3 up to the limit of overflow towards the column head 2 (except for Example 1).

When all of the reactants have been introduced into the reactor, the mixture is brought to 85° C. (Examples 1 to 3) or to 85°–100° C. (Examples 4 and 5) at $3.3 \times 10_4$ Pa (250 mmHG) and the desired temperature is regulate by applying the pressure required to maintain this temperature.

The reaction is considered to be complete when the residual content of acrylic acid reaches 0.5%. After returning to atmospheric pressure, the crude is cooled to 40° C. and neutralized with aqueous 8% sodium hydroxide solution with an NaOH/total acidity molar ratio of 1.05.

Example 1 (comparative)

The heteroazeotropic mixture is withdrawn completely, without any refluxing. A very high content of AA is observed in the aqueous phase.

Example 2 (comparative)

A withdrawal at constant interphase level is performed. A very high content of AA in the reaction water is observed.

Example 3

A delayed withdrawal is performed. A low content of AA in the reaction water is observed.

Example 4

The process is performed as n Example 3, but at increased temperature, which makes it possible to obtain a shorter reaction time while retaining a low passage of acrylic acid in the reaction water.

Example 5

A withdrawal at constant interphase level is performed, with continuous introduction into the decanter of some of the alcohol provided for the reaction. This procedure also gives good results as regards the content of AA in the reaction water.

This manner of performing the process during the reaction is compatible with a continuous synthesis of the 2EHA.

The results of these Examples 1 to 5 are presented in Table 1 below.

Example 6

The reaction is carried out at a temperature of 85° C. A delayed withdrawal is carried out without recycling of 2EHA. A low content of AA in the reaction water and a good reaction time are observed.

Example 7 (comparative)

The process is performed as in Example 6, but the refluxing is provided by introduction of alcohol at the column head and not into the decanter, at a flow rate which is a function of the reaction time and is exactly identical to that of the condensed liquid at the column head, thus perfectly simulating natural refluxing via the decanter. The results are marked poorer and considerable entrainment of AA in the reaction water is observed.

This therefore shows that the two effects (increase in the amount of liquid refluxed into the column and extraction of acrylic acid by the fresh alcohol present in the decanter) are complementary and necessary in order to reduce the content of acrylic acid in the reaction water.

Example 8

The process is performed as in Example 6, but with recycling of 2EHA. The results are equivalent to those of Example 6.

TABLE 1

| Example | 1 (Comparative) | 2 (Comparative) | 3 | 4 | 5 |
|---|---|---|---|---|---|
| Recycled ester/charge (%) | 0 | 0 | 15 | 18 | 18 |
| Reaction temperature (°C.) | 85 | 85 | 85 | 85–95 | 85–100 |
| Mode of withdrawal of the aqueous phase | Total withdrawal without reflux | Withdrawal at constant interphase level* | Delayed withdrawal | Delayed withdrawal | Continuous withdrawal, with further continuous addition of alcohol into the decanter |
| Initial content of the decanter | none | 2EHOH | 2EHOH | 2EHOH | 2EHOH |
| Volume of the condensed azeotropic mixture (liters) | 9 | 9 | 9 | 9 | 9 |
| Volume of the refluxed organic phase (liters) | | | | | |
| natural reflux of the decanter | 0 | 0.9 | 9 | 9 | 0.9 |
| addition of 2EHOH into the decanter** | 0 | 0 | 0 | 0 | 2.4 |
| Reflux/condensed heteroazeotropic mixture ratio (v/v) | 0 | 0.1/1 | 1/1 | 1/1 | 2.8/1 |
| Reaction time (min) | 240 | 270 | 390 | 300 | 300 |
| AA in the reaction crude (%) | 0.45 | 0.55 | 0.51 | 0.37 | 0.51 |
| AA in the reaction water | | | | | |
| AA/aqueous phase (%) | 12.7 | 14.5 | 1.8 | 0.7 | 2.2 |
| AA aqueous phase/initial AA (%) | 3.5 | 4.1 | 0.4 | 0.19 | 0.46 |

*without addition of alcohol
**no addition of 2EHOH at the head of the distillation column

EXAMPLES 6 to 14

The process is performed as for Examples 1 to 5, but in a heated reactor one liter in capacity. In order to perform certain examples, some of the alcohol provided for the reaction is introduced continuously into the decanter or at the column head, for all or part of the reaction.

Example 9

The process is performed as in Example 8, but starting with a decanter filled with an 80/20 by volume 2EHA/ 2EHOH mixture, in place of a decanter filled with 2EHOH. Slightly more entrainment of AA in the reaction water is observed, which is explained by a more favorable-level of extraction of AA in the organic phase in the case of the alcohol than in the case of the ester.

Example 10

The process is performed as in Example 8, but at a reaction temperature of 85°–100° C., with delayed withdrawal of the reaction water. Little entrainment of AA, a greatly reduced reaction time and increased productivity are observed.

Example 11 (comparative)

The process is performed as in Example 10, but with withdrawal of the azeotropic mixture at constant interphase level and continuous sending of the complement of alcohol to the column head, in order to ensure the same level of reflux. As a result of not passing via the decanter, the entrainment of AA in the reaction water is strongly reduced.

Example 12 (comparative)

The process is performed as in Example 10, but with total withdrawal of the condensed azeotrope and continuous sending of the complement of alcohol to the column head, in order to ensure the same level of reflux. The same observations as in Example 11 are made.

Example 13

The process is performed as in Example 10, with delayed withdrawal of the reaction water, but also with continuous supplementary addition of fresh alcohol into the decanter. Very good results in terms of entrainment of AA in the reaction water are observed, which are enhanced by the continuous renewal of the fresh alcohol.

Example 14

The process is performed as in Example 12, but with withdrawal at constant level of the reaction water. Equivalent results are obtained.

TABLE 2

| Example | 6 | 7 (comparative) | 8 | 9 | 10 | 11 (comparative) | 12 (comparative) | 13 | 14 |
|---|---|---|---|---|---|---|---|---|---|
| Recycled ester/charge (%) | 0 | 0 | 15 | 15 | 20 | 20 | 20 | 20 | 20 |
| Reaction temperature (°C.) | 85 | 85 | 85 | 85 | 85–100 | 85–100 | 85–100 | 85–100 | 85–100 |
| Mode of withdrawal of the aqueous phase | Delayed withdrawal | Total withdrawal with refluxing by introduction of 2EHOH at the column head | Delayed withdrawal | Delayed withdrawal | Delayed withdrawal | Withdrawal at constant interphase level, with further continuous addition of alcohol at the column head | Total withdrawal with refluxing by introduction of 2EHOH at the column head | Delayed withdrawal, with further continuous addition of alcohol into the decanter | Continuous withdrawal, with further continuous addition of alcohol into the decanter |
| Initial content of the decanter | 2EHOH | 2EHOH | 2EHOH | 2EHOH/2EHA 20/80 | 2EHOH | 2EHOH | 2EHOH | 2EHOH | 2EHOH |
| Volume of the condensed azeotropic mixture (ml) | 73.5 | 73.5 | 73.5 | 73.5 | 73.5 | 73.5 | 73.5 | 73.5 | 73.5 |
| Volume of the refluxed organic phase (ml) | | | | | | | | | |
| natural refluxing of the decanter | 73.4 | 0 | 73.4 | 73.4 | 73.4 | 8.7 | 0 | 73.4 | 8.7 |
| addition of 2EHOH into the decanter | 0 | 0 | 0 | 0 | 0 | 0 | 0 | 129.4 | 194.2 |
| addition of 2EHOH at column head | 0 | 64.7 | 0 | 0 | 0 | 64.7 | 71.9 | 0 | 0 |
| Reflux/condensed azeotropic mixture ratio (v/v) | 1/1 | 0.9/1 | 1/1 | 1/1 | 1/1 | 1/1 | 1/1 | 2.8/1 | 2.8/1 |
| Reaction time (min) | 290 | 315 | 270 | 290 | 195 | 210 | 190 | 210 | 195 |
| AA in the reaction crude (%) | 0.48 | 0.36 | 0.47 | 0.41 | 0.32 | 0.4 | 0.38 | 0.35 | 0.33 |
| AA in the reaction water | | | | | | | | | |
| AA/aqueous phase (%) | 1.1 | 5.7 | 1.4 | 3.5 | 2.1 | 5.3 | 6.2 | 0.8 | 1.2 |
| AA aqueous phase/initial AA (%) | 0.27 | 1.35 | 0.34 | 0.88 | 0.52 | 1.22 | 1.65 | 0.2 | 0.3 |
| Yield 2EHA/AA (%) | 97.8 | 93.9 | 96.8 | 97.5 | 98.3 | 95 | 96.3 | 98.9 | 97 |

Examples 15 and 16

In order to demonstrate the efficiency of a re-extraction, in the washing column 6, of the residual AA entrained in the reaction aqueous phase by the neutralized crude reaction mixture, using this aqueous phase as washing water, an industrial column was simulated exactly by using an array of three laboratory mixer-decanters, each mixer-decanter stage representing a theoretical stage of an industrial washing column, and by performing the following operations: placing of the aqueous phase obtained during the esterification reaction in intimate contact with the organic phase consisting of the neutralized crude reaction mixture in a mixing compartment, by means of a turbo-mixer; and separation into two phases, by gravity, of the emulsion formed, in a decanter compartment associated with each mixer. The two phases then pass, in countercurrent, into the adjacent stages.

Example 15

A crude mixture of the following composition is recovered from a reaction for the esterification of AA by 2EHOH formed in the laboratory under the optimum conditions described above:

2EHA: 91%;
2EHOH: 4%;
AA: 0.5%;
2-ethylhexyl hydrogen sulphate: 2.7%.

This mixture is neutralized with aqueous 8% sodium hydroxide solution, with a molar ratio of sodium hydroxide to all of the acidic species of 1.05. After separation of the two phases obtained, verification is made that the organic phase is free of AA and of 2-ethylhexyl sulphate.

The same reaction makes it possible to recover an aqueous phase in the decanter located at the head of the reaction column, the analysis of which phase is as follows:

$H_2O$: 98.2%;
2EHOH: 0.09%;
AA: 1.7%.

The organic phase consisting of the neutralized reaction crude is sent into the mixing compartment of the first stage of liquid—liquid extraction, whereas the reaction aqueous phase is introduced into the compartment of the third stage of extraction. The weight ratio of the organic phase to the aqueous phase is 3.3/1. The two phases meet in countercurrent in each stage.

The organic phase leaves via the mixing compartment of the third stage: it contains 0.46% of AA. The aqueous phase leaves via the mixing compartment of the first stage. It contains 0.15% of AA.

The extraction yield, expressed as the ratio of AA recovered in the organic phase to the AA introduced via the entering aqueous phase is 88% at the outlet of the third stage.

This yield of extraction, per stage, thus breaks down as:

1 stage: 63%;
2 stages: 85%;
3 stages: 88%.

Example 16

In a second example, the same conditions are retained, except for the fact that the molar ratio of sodium hydroxide to acidity is adjusted such that the AA contained in the reaction crude (7.02 g) is only partially neutralized by the sodium hydroxide in the first step.

The crude mixture has the following composition:

2EHA: 90%;
2EHOH: 4.5%;
AA: 0.95%;
2-ethylhexyl hydrogen sulphate: 2.6%.

The aqueous phase withdrawn in the decanter located at the head of the reaction column has the following composition:

$H_2O$: 98.2%
2EHOH: 0.09%;
AA: 1.7%.

After neutralization, the high acidity due to the 2-ethylhexyl hydrogen sulphate is totally neutralized, and a content of 0.7% AA remains in the crude, i.e. 4.15 g of AA. 59% of the AA contained in the crude initially are thus recovered.

This crude is sent into the array of the three mixer-decanters, as has been described above, in counter-current to a reaction aqueous phase containing 1.72% of AA (i.e. 3.1 g of AA), with a weight ratio of the organic phase to the aqueous phase of 3.3/1.

An organic phase leaving via the mixing compartment of the third stage, which contains 0.89% of AA (i.e. 5.23 g of AA); and an aqueous phase leaving via the mixing compartment of the first stage, which contains 1.07% of AA (i.e. 2.02 g of AA), are recovered.

The extraction yield, expressed as the ratio of the AA recovered in the organic phase to the AA introduced via the entering flows (reaction aqueous phase and neutralized crude) is 72% at the outlet of the third stage.

We claim:

1. In a process for the manufacture of an acrylic acid ester, said process comprising reacting said acid and a primary or secondary aliphatic monoalcohol having a number of carbon atoms greater than or equal to 5, in the presence of an acid as esterification catalyst and of a polymerization inhibitor, the alcohol being capable of forming a heteroazeotrope with water, entraining the water formed by the esterification reaction by distillation in a column in the form of a heteroazeotropic mixture with the alcohol, which mixture contains an amount of unreacted acrylic acid, condensing said mixture and phase separating in order to give an upper organic phase which is recycled to the head of the distillation column and a lower aqueous phase which is withdrawn, the improvement comprising extracting the acrylic acid contained in the condensed heteroazeotropic mixture intended for phase separation with an esterfiying-alcohol-richmixture, returning the acrylic acid thus extracted to the head of the distillation column, as a constituent of the recycled organic phase, and increasing the level of reflux in the distillation column relative to natural reflux.

2. A process according to claim 1, wherein the esterification is carried out continuously, and the extraction operation is carried out in an extraction column (EC) supplied, at the head, with a condensed heteroazeotropic mixture (M), and, at the foot, with fresh alcohol.

3. A process according to claim 1, wherein the esterification is carried out continuously, and the extraction operation is carried out in a decanter (D) supplied, in an upper part of a supernatant organic phase (O), with a condensed heteroazeotropic mixture (M), and in a lower part of a lower aqueous phase (A), with fresh alcohol, and the process is performed so as to withdraw at constant interphase level in the decanter (D).

4. A process according to claim 1, wherein the esterification is carried out discontinuously, and the extraction operation is carried out in an extraction column (EC) supplied, at the head, with a condensed heteroazeotropic mixture (M), and, at the foot, with fresh alcohol.

5. A process according to claim 1, wherein the esterification is carried out discontinuously, comprising carrying out the extraction operation in a decanter (D) of such a size as to be able to receive at least all of the heteroazeotropic mixture (M) without withdrawing at the bottom of the said decanter (D); before starting the reaction, filling the decanter (D) of esterifying alcohol to the overflow level in the distillation column (DC); accumulating the condensed heteroazeotropic mixture (M), which is led into the upper part of the organic phase (O) which forms in the decanter (D), in the latter for all or part of the reaction, the volume of upper organic phase (O) displaced by the volume of accumulated heteroazeotropic mixture being refluxed (by R) to the head of the distillation column (DC); and when the reaction is complete, withdrawing the lower aqueous phase (A) and replacing the volume of the heteroazeotropic mixture removed by fresh alcohol for a subsequent esterification reaction.

6. A process according to claim 5, wherein the esterification is carried out discontinuously, an fresh alcohol is introduced into the decanter for all or part of the reaction.

7. A process according to claim 1, wherein the aqueous phase obtained after the extraction operation is directed to a downstream distillation column (9), from which light organic products at the head are recovered and waste water at the foot are discharged.

8. A process according to claim 1, further comprising extracting traces of acrylic acid contained in the aqueous phase (13) obtained after the separation operation and wherein said extraction is carried out in the washing column (6), with the reaction crude (17) freed of the catalyst and of all or part of the acrylic acid by neutralization.

9. A process according to claim 1, wherein the esterification reaction is carried out at a temperature from 80° to 130° C., at normal pressure or at reduced pressure.

10. A process according to claim 1, wherein the alcohol is 2-ethylhexanol.

11. A process comprising extracting acrylic acid contained in a condensed heteroazeotropic mixture of a primary or secondary $C_{5+}$- esterifying alcohol, acrylic acid acrylic acid ester and water produced by reaction of acrylic acid and esterifying alcohol and entrainment of reaction water by distillation, wherein said extraction is performed with said esterifying alcohol.

12. In a process for the manufacture of an acrylic acid ester, said process comprising reacting said acid and a primary or secondary aliphatic monoalcohol having a number of carbon atoms greater than or equal to 5, in the presence of an acid as esterification catalyst and of a polymerization inhibitor, the alcohol being capable of forming a heteroazeotrope with water, entraining the water formed by the esterification reaction by distillation in a column in the form of a heteroazeotropic mixture with the alcohol, which mixture contains an amount of unreacted acrylic acid, condensing said mixture and phase separating in order to give an upper organic phase which is recycled to the head of the distillation column and a lower aqueous phase which is withdrawn, the improvement comprising extracting the acrylic acid contained in the condensed heteroazeotropic mixture intended for phase separation with an esterifying-alcohol-rich mixture, returning the acrylic acid thus extracted to the head of the distillation column, as a constituent of the recycled organic phase.

* * * * *